United States Patent
Serafin, Jr.

(10) Patent No.: US 6,629,999 B1
(45) Date of Patent: *Oct. 7, 2003

(54) MODULAR JOINT

(76) Inventor: Louis A. Serafin, Jr., 3315 Berry Dr., Lakeport, MI (US) 48059

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/518,888

(22) Filed: Mar. 6, 2000

Related U.S. Application Data

(60) Provisional application No. 60/123,383, filed on Mar. 8, 1999.

(51) Int. Cl.[7] .................................................. A61F 2/38
(52) U.S. Cl. .................................................. 623/20.15
(58) Field of Search .......................... 623/20.15, 20.14, 623/20.24, 20.25, 20.26, 20.27, 20.28, 20.29, 20.34, 20.35

(56) References Cited

U.S. PATENT DOCUMENTS

| | | | |
|---|---|---|---|
| 3,868,730 A | * | 3/1975 | Kaufer et al. ............. 623/20.22 |
| 4,012,795 A | | 3/1977 | Dorre et al. ................... 3/1.91 |
| 4,224,697 A | * | 9/1980 | Murray et al. ............ 623/20.22 |
| 4,936,853 A | * | 6/1990 | Fabian et al. .................. 623/20 |
| 5,766,257 A | | 6/1998 | Goodman et al. ............ 623/20 |
| 5,776,201 A | * | 7/1998 | Colleran et al. ......... 623/20.25 |
| 5,954,770 A | * | 9/1999 | Schmotzer et al. ........... 623/20 |
| 6,099,570 A | * | 8/2000 | Livet et al. ............... 623/20.21 |
| 6,117,175 A | * | 9/2000 | Bosredon ................. 623/20.15 |

FOREIGN PATENT DOCUMENTS

| | | |
|---|---|---|
| EP | 0980679 | 2/2000 |
| EP | 0985386 | 3/2000 |
| GB | 3529894 | * 3/1987 |

OTHER PUBLICATIONS

ASTM–F–799–95 (1995).
ASTM–F–1537–94 (1994).
Serafin, Jr. U.S. Provisional Application No. 60/123,383 filed Mar. 8, 1999 (Specification).
Communication of Feb. 3, 2003 with Partial European Search Report, Sheet C, and Annex for EP 01302007.8–2310–.

* cited by examiner

*Primary Examiner*—Corrine McDermott
*Assistant Examiner*—Alvin Stewart
(74) *Attorney, Agent, or Firm*—Christopher John Rudy; Andrew Joseph Rudy

(57) ABSTRACT

Basic implantable joint is adapted such that addable component(s) thereto can be added to the basic joint without removal of the joint from the site to which it can be initially implanted to provide a modular joint. Other modular features to a basic implantable joint are provided as well. The modular joint can be, for example, that of the knee and include a basic, implantable femoral component, with the addable component(s) able to be added inter-condylarly, which, for example, can include an insertable rotation device with a swingable, depending male type part; intramedullary spike and/or posterior stabilizing stop.

31 Claims, 5 Drawing Sheets

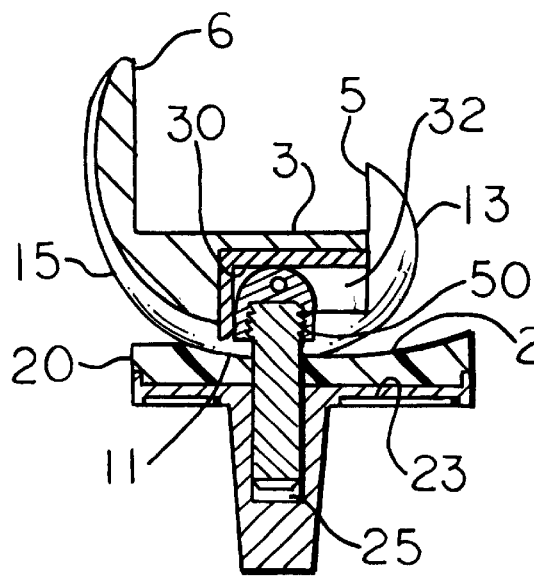
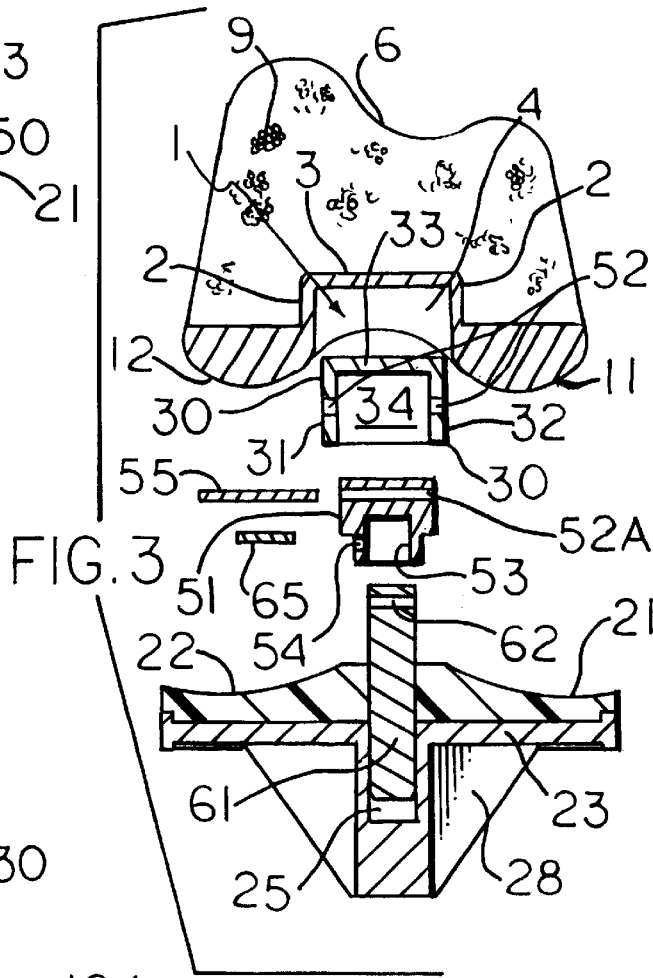
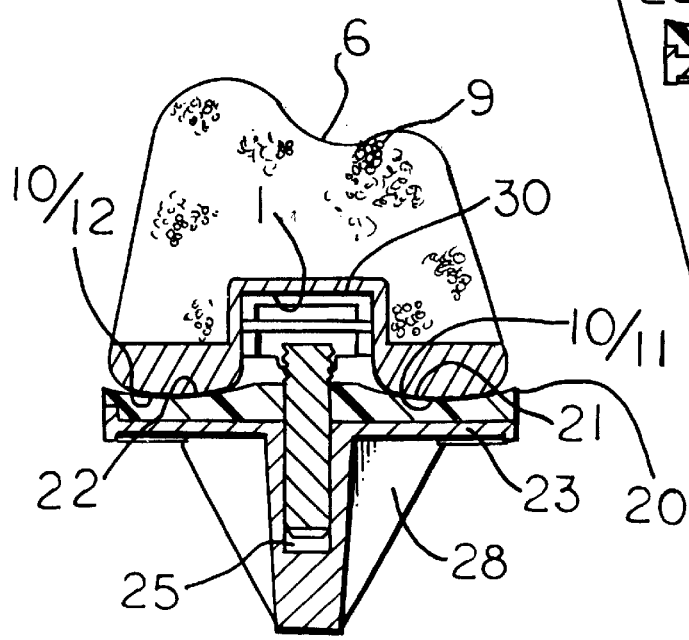

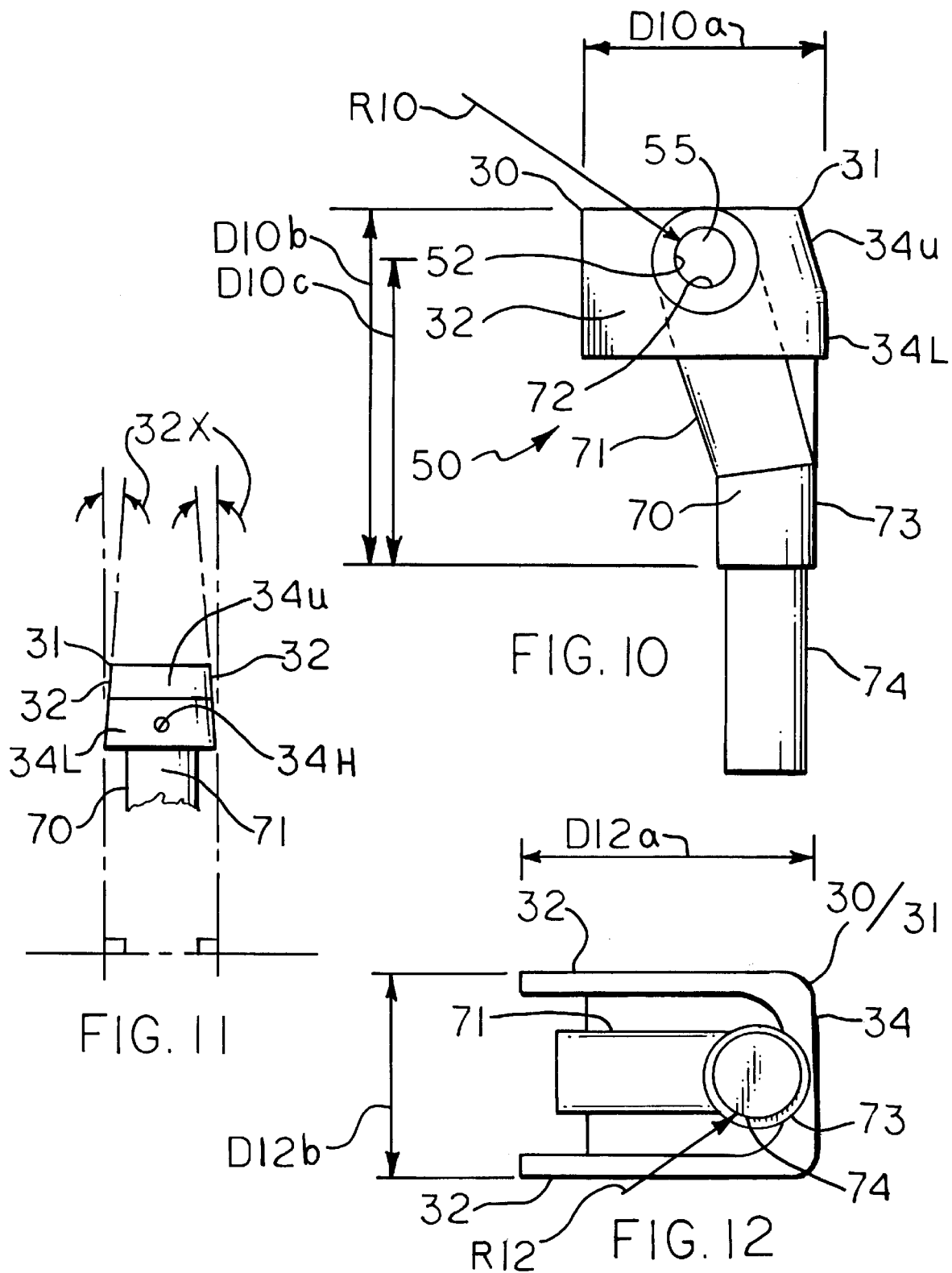

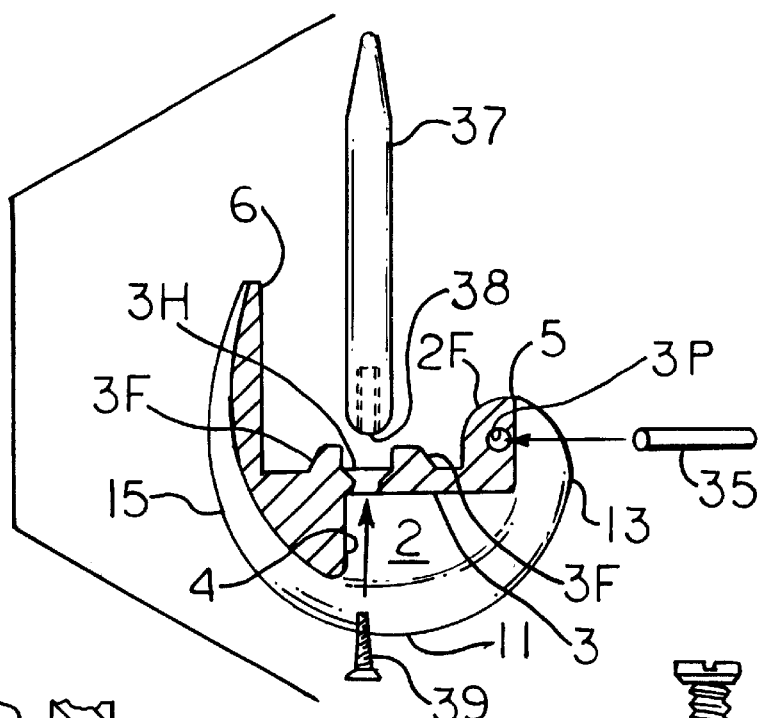
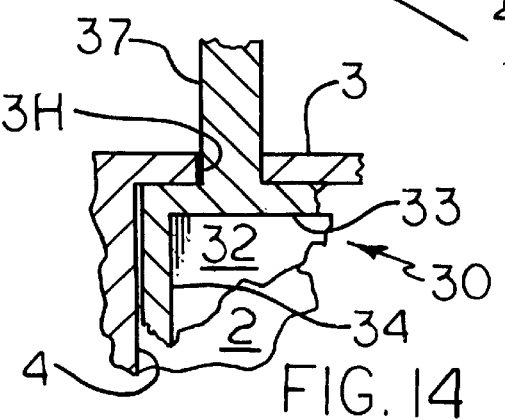
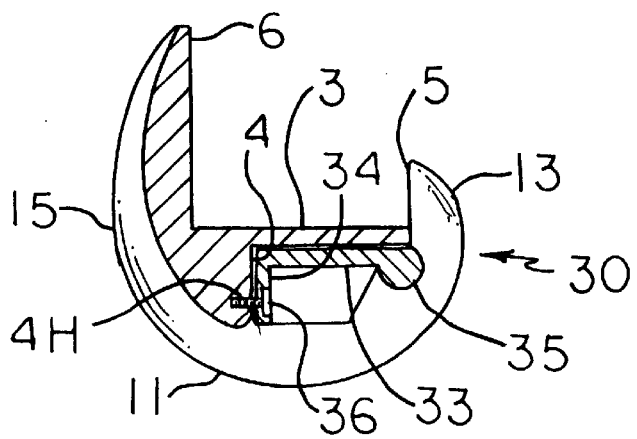
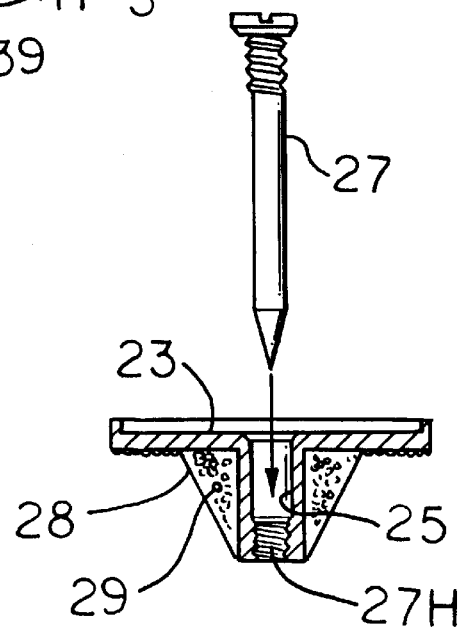
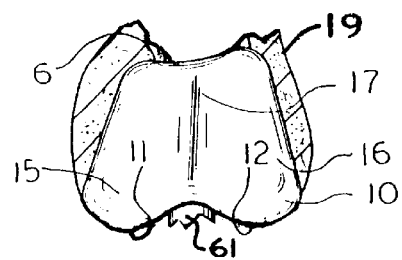

MODULAR JOINT

CROSS-REFERENCE CLAIM OF PRIORITY

This claims the benefit under 35 USC 119(e) of U.S. provisional application No. 60/123,383 filed on Mar. 8, 1999.

FIELD

The present invention concerns a modular joint. In a particular embodiment thereof, it concerns a prosthetic knee joint or component(s) therefor.

BACKGROUND

Various artificial joints and parts thereof are known.

A particularly useful artificial joint is disclosed by Goodman et al., U.S. Pat. No. 5,766,257 (Jun. 16, 1998). The same has natural load transfer.

A certain level of modularity exists among some known joints. For example, with total conventional hip prostheses, variously sized ceramic heads may be available for fixation to a femoral stem component. In the particular field of knee prostheses, it is known to provide insertable or thread-in, long, intramedullary spikes and adaptations therefor, in both femoral (proximal-facing adaptation) and tibial (distal-facing adaptation) components; and short, condyle-backing femoral spikes. However, such, in general, are not exchangeable after implantation, unless, for instance, the prosthesis would be removed and altered following its removal, which could have a profound, serious, negative impact on the patient.

It is always desirable to minimize the extent of surgical invasion and its potential for complications arising therefrom. See, e.g., Goodman et al.

SUMMARY

In general, the present invention provides a modular joint comprising a basic implantable joint adapted such that addable component(s) thereto can be added to the basic joint without removal of the joint from the site to which it can be initially implanted. Other modular features to a basic implantable joint are provided as well. In a particular, preferred embodiment, the modular joint is for the knee, for instance, comprising a basic, implantable femoral component, with the addable component(s) able to be added inter-condylarly, which, for example, can include an insertable rotation device with a swingable, depending male type part; intramedullary spike and/or posterior stabilizing stop.

The invention is useful in arthroplasty.

Significantly, by the present invention, an adaptable, versatile modular joint is provided. Even after implantation of the basic joint, addable component(s) can be added without removal of the basic joint, as may be required by the condition of the patient. Thus, surgical invasion from a future revision may be kept to a minimum, while the physician is provided with a series of progressive options in arthroplastic treatment.

Numerous further advantages attend the invention.

DRAWINGS

The drawings also form part of the present specification. With respect to the present drawings, which are not necessarily drawn to scale, the following is briefly noted:

FIG. 1 is a sagittal sectional view of a modular joint of the present invention, which is embodied as a prosthesis for a human knee.

FIG. 2 is a rear (posterior to anterior) sectional view of the modular joint of FIG. 1.

FIG. 3 is an exploded, rear (posterior to anterior) sectional view of a modular joint similar to that of FIGS. 1 & 2 employing pin type attaching of its axial pin (taper pin).

FIG. 10 is a side, elevational phantom type view of another addable component (preferred insertable rotation device with a swingable, depending male type part and topless housing) of a modular joint of the present invention.

FIG. 11 is a front (anterior to posterior) view of the component of FIG. 10.

FIG. 12 is a bottom, phantom type view of the component of FIGS. 10 & 11.

FIG. 13 is an exploded view of another embodiment of the present invention, with the basic joint (human femoral component) depicted in elevation and sagittal section.

FIG. 14 is a side, sectional view of another embodiment of a modular joint of the present invention, a human femoral component with a modular, intramedullary spike.

FIG. 15 is a sagittal sectional view of another embodiment of a modular joint of the present invention, a human femoral component with a modular posterior stabilizing stop.

FIG. 16 is an exploded view of another embodiment of a modular joint of the present invention (tibial tray insert with tibial intramedullary spike addable after the basic joint has been implanted) with the basic tibial tray a rear (posterior to anterior) view.

FIG. 17 is a front view (anterior to posterior direction) of a modular joint of the invention, which is embodied as a femoral component for a left human knee such as present within FIGS. 1–5, 13 and 15, and which shows additional articulating surfaces.

ILLUSTRATIVE DETAIL

The invention can be further understood through the present detail, which may be read in view of the drawings. Such is to be taken in an illustrative, and not necessarily limiting, sense.

The complete specifications of the application No. 60/123,383 of Serafin, Jr., and the U.S. Pat. No. 5,766,257 to Goodman et al., are incorporated herein by reference.

In reference to the present drawings, the modular joint of the present invention is depicted for purposes of illustration as a left knee prosthesis for a human being, or as addable components for the prosthesis. A corresponding joint for the right human knee could be a mirror image of the left. Other prostheses, especially other ginglymous type joints, for example, the elbow or knuckles, may be provided by appropriate analogy to the knee in the practice of the invention. Modular joints of the invention also may be provided with suitable modification for implantation in animals. Each patient is different, and thus, each may be custom fitted. Joints of the invention may be provided for mechanical or robotics applications as well. Accordingly varied can be the joint designs, shapes, and sizes, and the materials employed in the practice of the invention.

Figure 4:
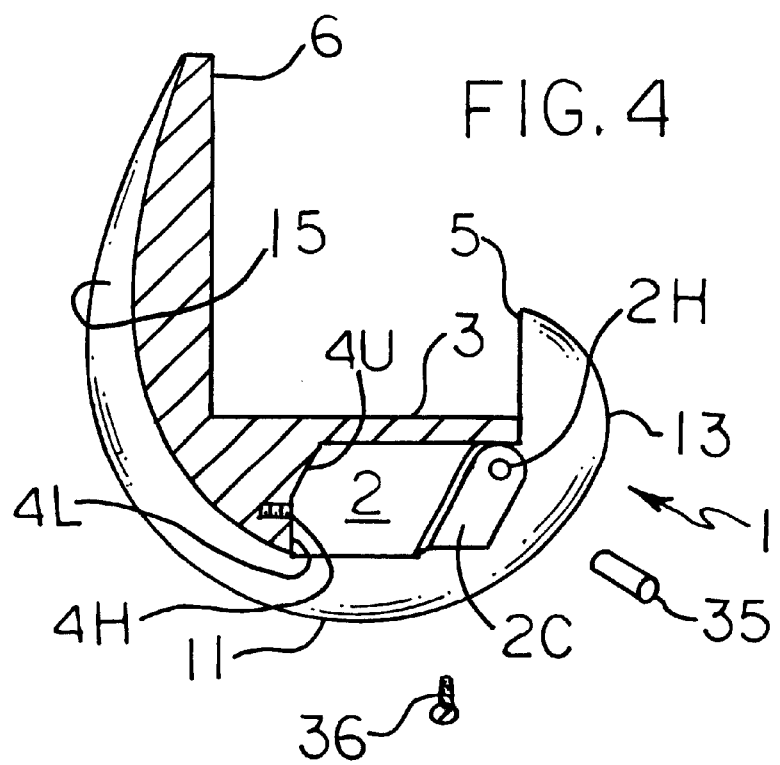
FIG. 4 is an exploded, sagittal sectional view of another embodiment of a basic joint portion (femoral component for a human knee) of a modular joint of the present invention.
Figure 5:
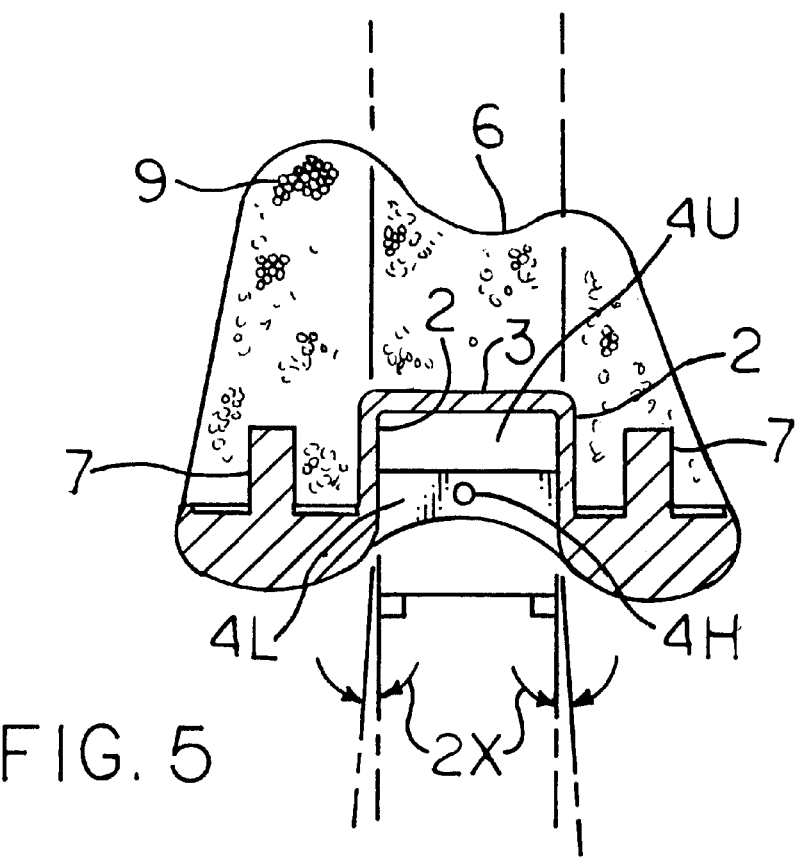
FIG. 5 is a rear (posterior to anterior) sectional view of the basic joint portion of FIG. 4.

With more particular respect to the present drawings, a modular joint component can be, say, in the form of a "box" and include receiving housing 1 which can have opposing (side) walls 2, top 3, and another insert restraining (front) wall 4, which may be opposed or not by another wall. Hole(s) may be provided in the walls, for example, top hole 3H and/or posterior stabilizing member accommodating hole 3P, which may be supported with proximal top flange 3F and side wall flange 2F, respectively (FIG. 13) or not be supported beyond that which the top wall 3 simply provides (FIG. 14); and addable module securing screw hole 4H (FIGS. 4, 5 & 15) which may otherwise be not threaded, say, for insertion of a pin rather than a set screw 36. As another possible option, channels or slots such as channel 2c may be provided in opposing walls 2, and an axle or rod, for instance, posterior stabilizing rod 35, may be guided into place near the top 3 of the housing 1 and secured there by insertion of screws or pegs, for instance, set screw 36, into hole 2H (FIG. 4). As is known in the art, a hole or channel may be capped with a suitable closure (not illustrated) such as a polyethylene cap when not taken advantage of. Preferably, the walls 2 are tapered, for instance, for a Browne & Sharpe taper, say, with a 1.5- to 2-degree angle 2X. Addable modules 30 (35, 37, 50) beneficially correspond to the housing 1 shape. Although a boxlike housing 1 and boxlike addable modules 30 are depicted, other shapes may be employed. For instance, the addable, modular "box" may be round, say with one flat side to keep the "box" from shifting. Such an addable "box" is advantageously inserted into a correspondingly shaped receptacle, say, in a femoral component implant for the knee. Returning to the present drawings, the housing 1 may have substantially planar walls (FIGS. 1–3) or have one or more walls in planar parts joined at an angle such as with the wall 4 (FIGS. 4 & 5) which has lower portion 4L and upper portion 4U. Corresponding addable modules 30 may be selected to conform to these housings 1. Compare, FIGS. 1, 3, 6, 7, 13 & 15 versus FIGS. 4, 5 & 10–12. Preferably, the addable component(s) can be added after the basic joint has been implanted in the patient—without the removal of the joint. Among such, desirably, the addable component(s) are able to be added inter-condylarly, which, for example, can include the inferiorly insertable rotation device with a swingable, depending male type part 50 (FIGS. 1–3, 6, 7 & 10–12); intramedullary femoral spike 37 (FIG. 14) and/or posterior stabilizing stop 35 (FIG. 15). In the case of the latter, as is known in the art, the tibial component is provided with a spine, peg, post, or other hindering structure, for example, as part of a tibial tray liner, to be thrust up between the condyles so that, when the stop 35 contacts the upstanding tibial member, anterior sublaxation or dislocation during flexion of the knee is precluded. An addable component, which may be added after the initial surgery, also may include the simple expedient of inserting a rod (not illustrated) through an available opening such as hole 3H (FIGS. 13 & 14) or open hole 27H (FIG. 16) in an implanted basic joint to help set a postoperative fracture, or employment of a superiorly insertable, threadable tibial intramedullary spike 27 (FIG. 16).

In general, the basic femoral component in addition to the addable component adaptation(s) can include posterior flange 5; anterior flange 6; articular/condylar surface 10 which generally includes inferior, medial condyle 11; inferior, lateral condyle 12; posterior, medial condyle 13; posterior, lateral condyle (not illustrated in present drawings); anterior, medial condyle 15; anterior, lateral condyle (not illustrated in present drawings); and so forth. On the superficial side of the anterior flange 6 can be provided trochlear surface 17, i.e., the trochlea, on which the actual or an artificial patella, i.e., the knee cap (not depicted), may generally ride. The femoral component for the knee generally is useful for surgical attachment to femoral bone stock 19. A set of condyle-backing femoral spikes 7 and/or porous coating 9 such as of pore-coated metal may be provided.

The basic tibial component in addition to the addable component adaptation(s) can include articulating surface providing substance (tibial tray liner) 20 such as of ultra high molecular weight polyethylene (UHMWPE); articulating/condylar mating surfaces 21 (medial) and 22 (lateral); tibial tray 23; tibial tray liner stop/clip 24; rotation device/axial pin receiving receptacle or hole 25. Metal-on-metal articulation may be provided by making the tibial component and its articulating surface 21 entirely of metal. Optionally, the basic tibial component may also contain the tibial spike receiving hole 27C (FIGS. 8 & 9) or 27H (FIG. 16); supporting flanges 28 and/or pore coating 29 (FIG. 16). As well, the basic tibial component may contain a set of hole(s) through the tibial tray 23 through which bone screw(s) may be passed (not illustrated).

As previously alluded to, the preferable type of addable component 30 can be a spike 33/37 (FIG. 14) or a posterior restraining member containing module such as the box (FIG. 15) having rear posterior restraining bar 35 included therewith. A combination spiked and posterior restraining containing module may be made and employed, or a combination spiked and rotating member containing module may be made employed. Generally, the presence of a posterior restraint obviates the effective use of the rotating member.

Figure 6:
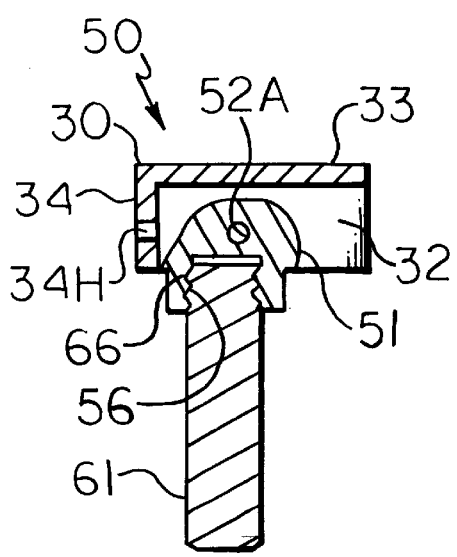
FIG. 6 is a sagittal sectional view of the addable component (insertable rotation device with a swingable, depending male type part) of the modular joint of FIGS. 1 & 2.
Figure 7:
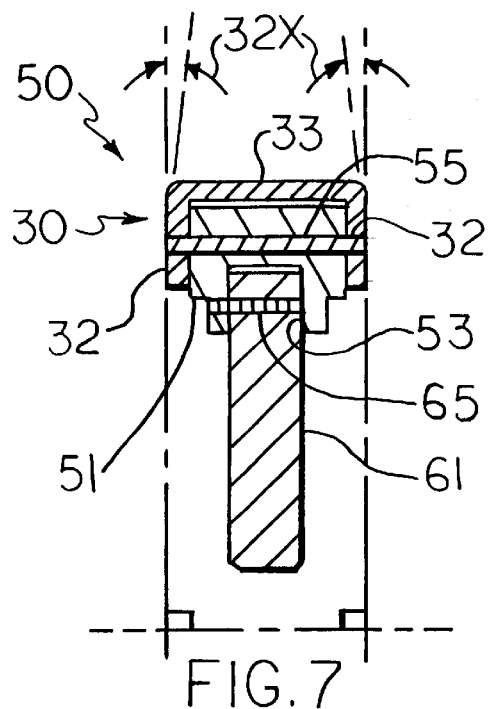
FIG. 7 is a rear (posterior to anterior) sectional view of the addable component (insertable rotation device with swingable, depending male type part) of the modular joint of FIG. 3.

Further, the addable component 30 of an inferiorly insertable rotation device with a swingable, depending male type part 50, in general, can include housing 31 having side walls 32; top wall 33 (FIGS. 1–3, 6 & 7), which may be eliminated in certain embodiments (FIGS. 10–12); and front wall 34. Thus, the top 33 of a modular "box" is optional. In fact, a preferred embodiment (FIGS. 10–12) is "topless." However, a top may impart structural stability, if required, and/or provide for another location to secure another component (e.g., FIG. 14, femoral intramedullary spike) or provide a site for fastening of the "box" to its corresponding receptacle. Holes 52 in the side walls 32 accommodates hinge pin (axle) 55. Pivot block (rotation member) 51 has hole 52A, which continues along the direction of the holes 52; taper pin cup 53; and punch pin hole 54. The axle 55 passes through the holes 52 & 52A, providing a pivot for the rotation member 51. The taper pin cup 53 may be smooth walled, tapered, say, with a Morse taper (FIGS. 3 & 7), or be provided with threads 56 (FIGS. 1, 2 & 6). Taper pin 61 is inserted into the cup 53, and may be secured in place with punch pin 65 (FIGS. 3 & 7) or with threads 66 (FIGS. 1, 2 & 6). Preferably, however, the part 50 is of one-piece construction 70 with block like upper rotation member portion 71 being made from the same piece as middle leg portion 73 and lower restraining post portion 70, the latter two being in general cylindrical, with the restraining post closely conforming in shape to the receptacle 25 of the tibial component. Axle hole 72 may be provided in the upper portion 71 to accommodate passage of the axle 55. Alternatively, the rotation member portion may be made integrally of one-piece construction with a built-in axle member appearing as opposing posts on either side of the member 71, and the same fit into a housing 31 by bending the housing around to fit. Also, the housing 31 may include shaped front panels 34L (lower) and 34U (upper). The hole 34H may be employed to secure the unit 50 into the femoral component through a screw or pin (passed into the hole 4H). To provide for the restraining taper, for example, the aforementioned Browne & Sharpe taper, the sides 32 are tapered appropriately, say, at about a 1.6- to 2.1-degree angle 32X (FIG. 11). The basic operational principles of an installed rotating member module parallel those of the artificial joint of the said patent to Goodman et al.

Module-in-module capability may be provided. For instance, the present invention can accommodate box-in-box capability. For example, the spike module 30/37 (FIG. 14) may be made to be able to receive a further module such as a posterior stabilizing member module such as the module 35/50 or receive an inferiorly insertable rotation device with a swingable, depending male type part such as the module 30/50 or 30/70.

Alternatively, a previously installed module may be removed before installing another module. In this connection, a pry slot (not illustrated) may be provided to the addable component module to assist in its removal.

Figure 8:
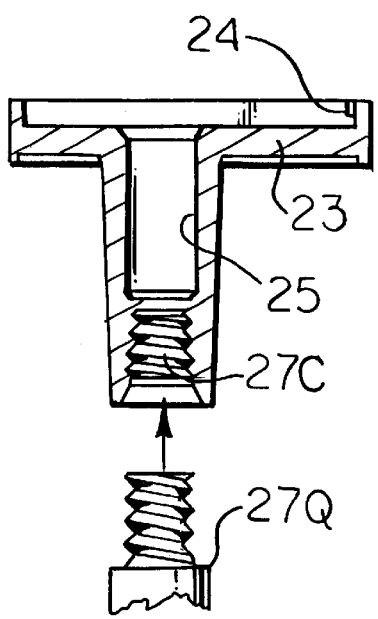
FIG. 8 is an exploded view of another embodiment of a modular joint of the present invention (tibial tray insert) with the basic tibial tray a rear (posterior to anterior) view.
Figure 9:
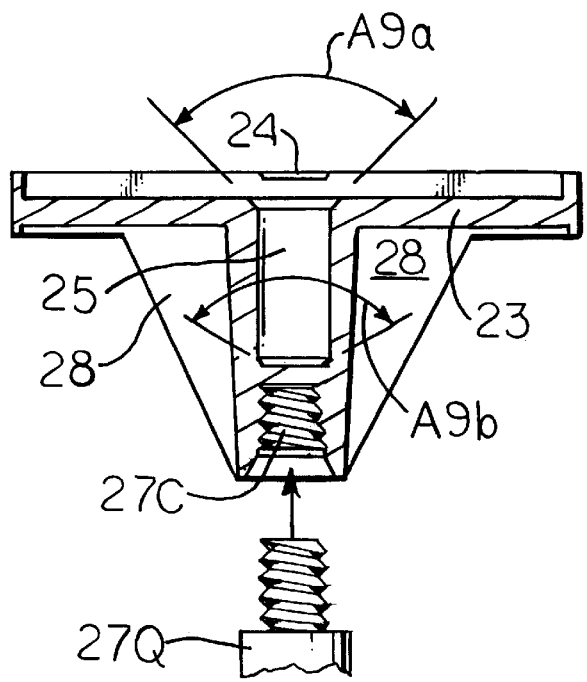
FIG. 9 is an exploded view of the joint of FIG. 8 again with the basic tibial tray being a rear (posterior to anterior) view.

Other adaptations for other insertable modular components can be provided for such as, for example, a separate posterior stabilizing rod 35, which may be inserted into the hole 3P (FIG. 13); a superiorly positionable femoral intramedullary spike 37 into the hole 3H, which spike has internal threads 38 so that it may be secured with screw 39; or an inferiorly positionable tibial spike 27Q, which spike has external threads for screwing into capped hole 27C (FIGS. 8 & 9). However, these other adaptations and insertable modular components may not be so readily insertable after the basic joint has been implanted.

The addable component(s) may be added as may be indicated for a particular patient.

Further exemplary dimensions can include those which follow:

| Feature Identity | Dimension |
|---|---|
| A9a (FIG. 9) | 90-degree angle. |
| A9b (FIG. 9) | 118-degree angle. |
| D10a (FIG. 10) | 0.9602-inch distance. |
| D10b (FIG. 10) | 1.7073-inch distance. |
| D10c (FIG. 10) | 1.4375-inch distance. |
| R10 (FIG. 10) | 0.1500-inch radius. |
| D12a (FIG. 12) | 1.0703-inch distance. |
| D12b (FIG. 12) | 0.8509-inch distance. |
| R12 (FIG. 12) | 0.1875-inch radius. |

Suitable materials and methods can be employed to make the modular joint of the present invention, and the basic joint can be fashioned according to an anatomical foundation. See, e.g., the specification of the patent to Goodman et al. Thus, metals, ceramics, and plastics, to include engineering plastics, may be employed in the practice of the present invention. Preferably, however, metal is substantially used throughout, except, for example, for a tibial tray liner, again say, which may be of the UHMWPE, or for closures, and again say, which may be made of a suitable polyethylene material. More preferably, in total joint arthroplasties, the same metal is used for both joint components, for example, femoral and tibial components of the knee. Cobalt is a preferred metal or alloy base, especially when provided according to the well known ASTM F-799 or ASTM F-1537 standards.

Beneficially, the modular joint of the present invention is constructed along a basic joint foundation which can provide for natural load transfer. See, e.g., present FIGS. 1–16. See also, the specification of the patent to Goodman et al.

Accordingly, among other embodiments in the practice of the present invention, the following is noted: in an artificial joint, which generally has natural load transfer capability, which includes a first component including a first articular surface and a rotation device, wherein the rotation device includes a swingable, depending male-type part; and a second component including a second articular surface for mating with the first articular surface, and a rotation device receptacle, wherein the rotation device receptacle includes a female-type part—with the first component matable to the second component through male-female cooperation of the rotation device and the rotation device receptacle, and wherein the first component can cooperate with the second component in contact of the first and second articular surfaces and in articulation of the joint when the first component is mated to the second component, wherein the first and second articular surfaces are such that they can have anatomical gliding contact against one another during anatomical rotation in addition to anatomical flexion and extension—the improvement can include an adaptation such that at least one addable component can be added to the basic joint without removal of the joint from a site to which it can be initially implanted. Also noted along the foregoing lines is the following embodiment of the present invention: in an artificial femoral component for a knee, which includes the following:

a femoral component frame, which includes two side walls connected to a front wall, the same being connectable in proximal and deep directions to distal condylar, posterior and anterior flanges, with the distal flange connected to the posterior and anterior flanges;

a smooth condylar surface of generally convex geometry connected to the femoral component frame in distal and superficial directions, which includes an inferior, medial condyle; an inferior, lateral condyle; a posterior, medial condyle; a posterior, lateral condyle; an anterior, medial condyle; and an anterior, lateral condyle; plus a trochlear surface on a superficial side of the anterior flange, on which a trochlea may generally ride; the condylar surface being such that an inter-condylar notch is present between medial and lateral condyles; and a rotation device connected to the femoral component frame,
which includes the following:
an angular rotation member having a rotation member hole in a proximal extremity thereto, which hole spans the rotation member in a medial to lateral direction, which rotation member about a distal extremity thereof can be inserted into a corresponding receptacle in a tibial tray; and
an axle passing through the hole which spans the rotation member and is connected to a frame through holes in side walls thereof;
the improvement can include as the rotation device a modular, inferiorly insertable rotation device, which can be inserted into and removed from a corresponding receptacle in the femoral component frame, wherein the angular rotation member is connected to the axle which is connected to walls of the modular, inferiorly insertable rotation device by holes in the walls through which the axle passes.

CONCLUSION

The present invention is thus provided. Various features, parts, subcombinations and combinations may be employed with or without reference to other features, parts, subcombinations or combinations in the practice of the invention, and numerous adaptations and modifications can be effected within its spirit, the literal claim scope of which is particularly pointed out as follows.

I claim:

1. A modular joint comprising a basic implantable joint structured to function as a first complete joint, which contains an adaptation configured such that at least one addable component can be added to the basic joint to form a second complete joint without removal of the joint from a site to which it can be initially implanted.

2. The joint of claim 1, which is a ginglymous type joint.

3. The joint of claim 2, having module-in-module capability.

4. The joint of claim 3, having box-in-box capability.

5. The joint of claim 2, which is a knee joint prosthesis.

6. The joint of claim 3, which is a knee joint prosthesis.

7. The joint of claim 4, which is a knee joint prosthesis.

8. The joint of claim 5, which is has at least one joint component selected from the group consisting of an implantable femoral component and an implantable tibial component, wherein at least one of said at least one joint component contains an adaptation such that at least one addable component can be added thereto without removal of the joint component from a site to which it can be initially implanted.

9. The joint of claim 8, wherein said joint component includes said femoral component, and said at least one addable component can be added inter-condylarly.

10. The joint of claim 9, wherein said at least one addable component is selected from the group consisting of an insertable rotation device with a swingable, depending male type part; an intramedullary spike; and a posterior stabilizing stop.

11. The joint of claim 10, wherein said at least one addable component includes said rotation device, wherein said rotation device is inferiorly insertable, and mounted in an insertable box for insertion into a corresponding receiving housing of said femoral component.

12. The joint of claim 11, which also includes said tibial component, and there is metal-on-metal articulation by having articulating surfaces of said femoral component and said tibial component made of metal.

13. In an artificial joint, which generally has natural load transfer capability, which includes a first component including a first articular surface and a rotation device, wherein the rotation device includes a swingable, depending male-type part; and a second component including a second articular surface for mating with the first articular surface, and a rotation device receptacle, wherein the rotation device receptacle includes a female-type part—said first component matable to said second component through male-female cooperation of the rotation device and the rotation device receptacle, and wherein said first component can cooperate with said second component in contact of the first and second articular surfaces and in articulation of the joint when said first component is mated to said second component, wherein said first and second articular surfaces are such that they can have anatomical gliding contact against one another during anatomical rotation in addition to anatomical flexion and extension—the improvement which comprises an adaptation such that at least one addable component can be added to the basic joint, which is structured to function as a first complete joint, to form a second, complete configuration of the joint without removal of the joint from a site to which it can be initially implanted.

14. The joint of claim 13, which is a knee joint prosthesis having femoral and tibial components, and said at least one addable component includes at least one intramedullary spike.

15. The joint of claim 14, which is a knee joint prosthesis having femoral and tibial components, and said at least one addable component includes as the rotation device a modular, inferiorly insertable rotation device.

16. The joint of claim 13, which is a knee joint prosthesis having femoral and tibial components, and said at least one addable component includes as the rotation device a modular, inferiorly insertable rotation device.

17. The joint of claim 13, wherein said first and second articular surfaces are made of metal so as to provide metal-on-metal articulation.

18. In an artificial femoral component for a knee, which includes the following:

a femoral component frame, which includes two side walls connected to a front wall, the same being connectable in proximal and deep directions to distal condylar, posterior and anterior flanges, with said distal flange connected to said posterior and anterior flanges;

a smooth condylar surface of generally convex geometry connected to the femoral component frame in distal and superficial directions, which includes an inferior, medial condyle; an inferior, lateral condyle; a posterior, medial condyle; a posterior, lateral condyle; an anterior, medial condyle; and an anterior, lateral condyle; plus a trochlear surface on a superficial side of the anterior flange, on which a trochlea may generally ride; said condylar surface being such that an inter-condylar notch is present between medial and lateral condyles; and a rotation device connected to the femoral component frame, which includes the following:

an angular rotation member having a rotation member hole in a proximal extremity thereto, which hole spans the rotation member in a medial to lateral direction, which rotation member about a distal extremity thereof can be inserted into a corresponding receptacle in a tibial tray; and an axle passing through the hole which spans the rotation member and is connected to a frame through holes in side walls thereof;

the improvement which comprises as the rotation device a modular, inferiorly insertable rotation device, which can be inserted into and removed from a corresponding receptacle in the femoral component frame, wherein the angular rotation member is connected to the axle which is connected to walls of the modular, inferiorly insertable rotation device by holes in said walls through which the axle passes.

19. An addable component for a modular ginglymous type joint implant comprising a housing having at least one flat side; an axle attached to the housing for receiving a rotation member; and the rotation member received on and depending from the axle, the rotation member being a male type part—wherein the addable component can be added to the modular ginglymous type joint.

20. The addable component of claim 19, wherein the modular ginglymous type joint implant is a femoral component of a knee implant having lateral and medial condyles; the addable component is inferiorly insertable between said condyles of the knee implant, and the rotation member has a generally cylindrical lower restraining post portion which can be inserted into a closely conforming receptacle in a tibial component.

21. The addable component of claim 20, wherein the housing is boxlixe in shape.

22. An artificial femoral component for a knee, which comprises the following:
- a femoral component frame, which includes two side walls connected to a front wall, the same being connectable in proximal and deep directions to distal condylar, posterior and anterior flanges, with said distal flange connected to said posterior and anterior flanges;
- a smooth condylar surface of generally convex geometry connected to the femoral component frame in distal and superficial directions, which includes an inferior, medial condyle; an inferior, lateral condyle; a posterior, medial condyle; a posterior, lateral condyle; an anterior, medial condyle; and an anterior, lateral condyle; plus a trochlear surface on a superficial side of the anterior flange, on which a trochlea may generally ride; said condylar surface being such that an inter-condylar notch is present between medial and lateral condyles; and
- a receiving housing in the femoral component frame and generally between lateral and medial condyles, said receiving housing able to receive a modular component insert therein.

23. The component of claim 22, wherein said receiving housing is in the form of a box having opposing side walls, a top wall, and an insert restraining front wall.

24. The component of claim 23, wherein said side walls are tapered with respect to one another.

25. The component of claim 24, further having at least one hole in at least one of said side, top, and front walls.

26. The component of claim 23, further having at least one hole in at least one of said side, top, and front walls.

27. A modular joint comprising a basic implantable joint which has natural load transfer capability, which is structured to function as a first complete joint, and which contains an adaptation configured such that at least one addable component can be added to the basic joint to form a second complete joint without removal of the joint from a site to which it can be initially implanted.

28. The joint of claim 27, which is a ginglymous type joint.

29. The joint of claim 28, which is a knee joint prosthesis.

30. The joint of claim 29, wherein the joint component includes a femoral component, and the at least one addable component can be added inter-condylarly and is selected from the group consisting of an insertable rotation device with a swingable, depending male type part; an intramedullary spike; and a posterior stabilizing stop.

31. The joint of claim 29, wherein the at least one addable component is selected from the group consisting of an intramedullary spike and a posterior stabilizing stop.

* * * * *